United States Patent [19]

Akkerboom et al.

[11] 4,177,189
[45] Dec. 4, 1979

[54] PROCESS FOR THE PREPARATION OF HYDROXYPHOSPHINYLUREIDOBENZYL-PENICILLINS

[75] Inventors: Piet J. Akkerboom, Zoetermeer; Geertruida J. Löwer, Geleen; Willem J. Timp, Delft, all of Netherlands

[73] Assignee: Gist-Brocades N.V., Delft, Netherlands

[21] Appl. No.: 908,221

[22] Filed: May 22, 1978

[30] Foreign Application Priority Data

Jun. 1, 1977 [GB] United Kingdom ............... 23227/77

[51] Int. Cl.$^2$ .......................................... C07D 499/68
[52] U.S. Cl. ................................................. 260/239.1
[58] Field of Search ..................................... 260/239.1

[56] References Cited

U.S. PATENT DOCUMENTS

| 3,945,994 | 3/1976 | Bruynes et al. ............ 260/239.1 |
| 4,067,986 | 1/1978 | Bruynes et al. ............ 260/239.1 |

*Primary Examiner*—Gerald A. Schwartz
*Attorney, Agent, or Firm*—Hammond & Littell

[57] ABSTRACT

An improved process for the preparation in high yields of a compound of the formula

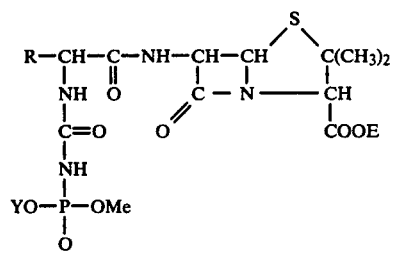

wherein R is an optionally substituted phenyl group, Y is selected from the group consisting of Me and a hydrocarbon, Me is a metal cation and E is selected from the group consisting of hydrogen and a metal cation comprising reacting a compound of the formula

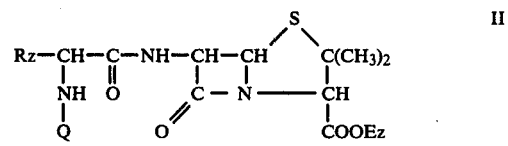

wherein Q is selected from the group consisting of hydrogen and a silyl protecting group, Rz is an optionally substituted phenyl with the proviso that any hydroxy group present on the phenyl are replaced by —OQz, wherein Qz is a silyl protecting group and Ez is a carboxyl protecting group, with a compound of the formula

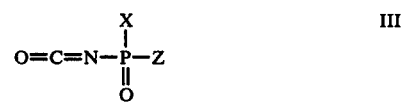

wherein Z is a halogen and X is selected from the group consisting of OY and Z at low temperatures under anhydrous conditions and carefully hydrolyzing the resulting product either with just enough water to remove protecting groups and hydrolyze the Z groups to hydroxy groups and, still under anhydrous conditions, reacting the compound obtained with an organic metal salt carrying a metal cation Me or, in the case wherein the organic solvent is water-insoluble, with an excess of water, followed by washing the mixture with water acidified to a pH of 0 to 3, extracting the organic phase with neutral water and forming a salt with a hydroxide or a salt carrying a salt-forming cation Me.

14 Claims, No Drawings

PROCESS FOR THE PREPARATION OF HYDROXYPHOSPHINYLUREIDOBENZYL-PENICILLINS

STATE OF THE ART

Processes for the preparation of hydroxyphosphinylureidobenzylpenicillins are already known. For example, Example 26 of British Pat. No. 1,464,551 describes the reaction of silylated D-6-(α-amino)-benzylcarboxamido-penicillanic acid or ampicillin with chloro (ethoxy) phosphinyl isocyanate [C₂H₅O-P(O)(Cl)NCO] in an organic solvent at a temperature of −65° to −70° C. The reaction mixture obtained is poured into iced water while simultaneously being neutralized with aqueous sodium hydroxide. After extracting the aqueous phase of the two-phase system formed with an organic solvent, the extract is evaporated to obtain about 5.5% yield of D-6-[α-{3-hydroxy(ethoxy-phosphinyl)-ureido}benzylcarboxamido]-penicillanic acid. This compound may be converted into a salt which appears to be more stable than the acid, but nevertheless, the yield remains low when calculated on the ampicillin compound used as starting material.

Using the same method but using as the starting material D-7-(α-amino)-benzylcarboxamido-desacetoxycephalo-sporanic acid (cephalexin), a much higher yield is obtained on the order of 61% according to Example 30 of the same patent. The cephalosporin is apparently more stable than the corresponding penicillin.

The disodium salt of D-6-[α-{3-(hydroxy(ethoxy)-phosphinyl)-ureido}benzylcarboxamido]-penicillanic acid may also be prepared by another process as described in Example 35 of the said British patent. Silylated ampicillin is reacted with benzyloxy(ethoxy)phosphinyl isocyanate [C₆H₅CH₂O(C₂H₅O)P(O)NCO] and the compound formed, after separation, is reduced with hydrogen using palladium-on-charcoal as a catalyst in the presence of sodium bicarbonate. Although this results in a much higher yield of the product, i.e. 50% based on the ampicillin starting material, the process has drawbacks in that palladized charcoal is expensive and the reduction step takes a considerable length of time.

By using anhydrous D-6-(α-amino)-p-hydroxybenzyl-carboxamido-penicillanic acid (amoxicillin) as the starting material as described in Example 5 of U.S. Pat. No. 4,067,986 it is possible to obtain the disodium salt of D-6-[α-{3-(hydroxy(ethoxy)phosphinyl)ureido}-p-hydroxybenzyl-carboxamido]-penicillanic acid using a similar reduction method with palladized charcoal as a catalyst. A yield of 74% was obtained calculated on the starting amoxicillin compound. However, the use of the expensive catalyst is again a drawback of this process.

OBJECTS OF THE INVENTION

It is an object of the invention to provide an improved process for the preparation of salts of hydroxyphosphinylureidopenicillins in good yields while avoiding the use of expensive palladized charcoal catalysts.

This and other objects and advantages of the invention will become obvious from the following detailed description.

THE INVENTION

The process of the present invention is a modification of the process of Example 26 of British Pat. No. 1,464,551 modified to obtain yields of 50% or more and comprises forming compounds of the formula

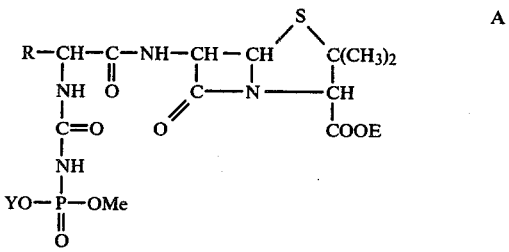

wherein R is phenyl optionally substituted with one or two members which may be the same or different, selected from the group consisting of hydroxy, lower alkyl and lower alkoxy, Y is selected from the group consisting of Me, lower alkyl, aryl(lower)alkyl and aryl in which the aryl is optionally substituted with at least one member lower alkyl, Me is a metal cation, preferably an alkali metal cation such as sodium or potassium or an alkaline earth metal cation such as calcium and E is selected from the group consisting of hydrogen and a metal cation, which may be the same or different from the metal cation Me, by reacting a compound of the formula

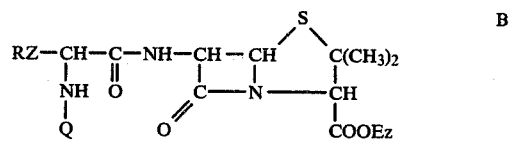

wherein Q is selected from the group consisting of hydrogen and a silicon atom carrying substituents selected from the group consisting of lower alkyl, lower haloalkyl, aryl, aralkyl and lower alkoxyalkyl and halogen atoms and preferably a trimethylsilyl, Rz has the same significance as R as defined above with the proviso that any hydroxy group(s) present on the phenyl group is (or are) replaced by a —OQz, wherein Qz has the same significance as Q as hereinbefore defined but excluding hydrogen, and Ez is a carboxyl-protecting group, e.g. a group Qz as hereinbefore defined, with a compound having the formula

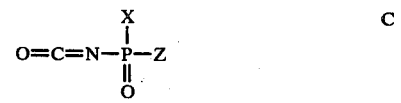

wherein Z is a halogen, preferably chlorine and X is selected from the group consisting of OY wherein Y is as hereinbefore defined and Z as hereinbefore defined at a temperature below 0° C., preferably from about −90° to about −40° C., more preferably from about −80° to about −60° C., under anhydrous conditions in an organic solvent medium, e.g. methylene chloride or ethyl acetate, and carefully hydrolyzing the product thus obtained either with an amount of water just sufficient to remove any protecting groups present in the intermediate product and to hydrolyze the group(s) Z to hydroxy group(s) and, still under anhydrous or substantially anhydrous conditions, converting hydroxy group(s) formed by hydrolysis of group(s) Z into group(s) OMe, wherein Me is as hereinbefore defined by an organic acid salt having a salt-forming cation Me, preferably an alkanoic salt with the alkanoyl containing 1 to 20 carbon atoms, preferably 5 to 10 carbon atoms or, in the case wherein the organic solvent used is one insoluble or substantially insoluble in water, with up to 100% excess, preferably 25 to 60% excess, of water, washing the mixture with water at a pH-value of 0 to 3, preferably 1 to 2, extracting the organic layer formed with water at a pH-value of 5 to 8, preferably 6.5 to 7.5 by adding a hydroxide or a salt having a salt-forming cation Me to convert the hydroxy group(s) formed by hydrolysis of groups Z into OMe and Ez into Me wherein Me is as defined above.

The term "lower" as used in connection with alkyl and alkoxy groups means that the groups contain 1 to 6 carbon atoms.

The salt formation when carried out in an organic medium is preferably carried out in organic solvents having moderately polar properties such as ethanol, butanol, acetone, ethyl acetate, methyl isobutyl ketone, methylene chloride or mixtures of two or more of these solvents. Examples of useful salts are salts of alkanoic acids such as acetic acid, propionic acid, butyric acids, pentanoic acids, hexanoic acids, heptanoic acids, octanoic acids, stearic acids, etc. Preferably, salts of 2-ethylhexanoic acid are used.

Due to the difference in the $pK_a$ of the P—OH and COOH groups, salt formation upon addition of an organic acid salt will first take place exclusively at the P—OH group(s), whereupon the formed partial salt precipitates and because of this the carboxylate ion will not be formed. Therefore, large amounts of the organic acid salt in excess of the amount calculated for salt formation of the P—OH group(s) are useless and should normally be avoided so as not to unnecessarily contaminate the final product. The precipitated partial salt is collected and converted into a di- or tri-salt, as the case may be, in any conventional manner such as by means of aqueous sodium carbonate.

In the case the hydrolyzed compound is washed with water before salt formation, care must be taken that the compound has been dissolved in an organic medium not soluble or substantially not soluble in water so that the compound remains in the organic phase during this washing. Examples of suitable solvents are methylene chloride, ethyl acetate, etc., but solvents like acetone should be avoided. The water may be acidified by a solution of an inorganic salt such as hydrochloric acid, phosphoric acid, nitric acid and sulfuric acid, etc. Hydrochloric acid is conveniently used. The salt formation afterwards may be effected by the use of solutions of a hydroxide or a salt of cations hereinbefore defined such as sodium hydroxide.

The starting compounds of formula II may be prepared by methods known per se. The phosphinyl isocyanates of formula III may be prepared, for example, as described by Narbut et al, Zh. Obshch. Khim. Vol. 38 (1968) page 1321 and Gubnitskaya et al, Zh. Obshch. Khim. Vol. 40 (1970) page 1205. By the term "methods known per se" as used in this specification is meant methods heretofore used or described in the chemical literature.

The cations E and Me are preferably non-toxic, pharmaceutically acceptable cations for penicillins, preferably alkali metals such as sodium, potassium or alkaline earth metals such as calcium.

The starting penicillin compounds from which the compounds of formula II are prepared contain a carboxylic acid or a carboxylic salt group and may contain other groups which may also interfere with the reaction. These groups are protected by a group Qz as hereinbefore defined by methods known per se. Preferably, silyl esters are prepared by reacting the free carboxyl group with, e.g. trimethylchlorosilane, N,O-bistrimethylsilylacetamide, trimethylsilylacetamide, dimethyldichlorosilane, bistrimethylsilylurea, bistrimethylsilylcarbamate or bistrimethylsilylsulfamate. When silylhalo compounds are used, it is preferred to carry out the silylation reaction in the presence of an acid binding compound such as triethylamine or ethylenediamine.

An advantage of the process of the present invention over the prior art methods previously discussed above for the preparation of hydroxyphosphinylureidobenzylpenicillins is that the reactions involved can all be carried out in one reaction vessel.

The compounds of formula I prepared by the process of the invention posssess antibiotic activity as described in British Pat. No. 1,464,551 and U.S. Pat. No. 4,067,986.

In the following examples, there are described several preferred embodiments to illustrate the invention. However, it should be understood that the invention is not intended to be limited to the specific embodiments.

EXAMPLE 1 disodium salt of
D-6-{α-[3-(hydroxy(ethoxy)-phosphinyl)ureido]-p-hydroxybenzylcarboxamido}-penicillanic acid 36.9 g (0.10 mole) of D-6-(α-amino)-p-hydroxybenzyl-carboxamido-penicillanic acid (amoxicillin) were silylated with a solution of 53.4 ml (0.22 mole) of N,O-bistrimethylsilylacetamide in 250 ml of methylene chloride and after cooling the solution to about −70° C., a solution of 17 g (0.10 mole) of $(C_2H_5O)PO(Cl)NCO$ (ethyl chlorophosphorus isocyanatidate) in 250 ml of dry acetone was added thereto dropwise. After completion of the addition, the mixture was stirred for 1½ hours and a mixture of 5.8 ml (0.32 mole) of water, 8.1 ml (0.10 mole) of pyridine and 250 ml of dry acetone were added at a temperature of −70° C. The temperature of the reaction mixture was then allowed to rise quickly to −40° C. and then slowly to −10° C. over a period of 2 hours to complete the hydrolysis of the chloride and protective silyl groups. 2 g of activated carbon were added to the mixture and after stirring for 10 minutes, the mixture was filtered. A solution of 16.8 g (0.10 mole) of sodium 2-ethylhexanoate in 200 ml of dry acetone was added to the filtrate at +5° C., and the mixture was stirred for 10 minutes at the same temperature, and for a further 15 minutes at ambient temperature. A precipitate was formed which was filtered off and was suspended in 1½ liters of dry acetone. The mixture was stirred for 45 minutes and the precipitate was then filtered off. The operation was repeated resulting in a much more pure product. The precipitate from the repeated operation was suspended in 750 ml of water and the suspension was cooled by the exterior application of ice and by nitrogen being bubbled through the mixture. The precipitate was dissolved by addition of 5.3 g of sodium bicarbonate at pH 6.8 and after freeze-drying of the solution, 33 g (58%) of the disodium salt of D-6-{α-[3-(hydroxy(ethoxy)phosphinyl) ureido]-p-hydroxybenzylcarboxamido}penicillanic acid were obtained containing only a trace of sodium 2-ethylhexanoate.

The physico chemical properties of the compound obtained are as follows:

IR Spectrum (KBr-disc, values in cm$^{-1}$): about 3200–3600 (broad and intensive), 2975, 2930 (sh), 1765, ±1650–1670, ±1610, 1550 (sh), 1515, 1460, 1400, 1375 (sh), ±1325, about 1240 (broad), 1180, 1135, 1085, 1050, 955, 900, 770.

PMR Spectrum (about 5:1 mixture of d$_6$-DMSO and DCO$_2$D, DSS as reference, δ-values in ppm): 1.25 (centre of two close triplets, J≈7.5 cps), 1.46 (s) and 1.59 (s) all together 9H; about 3.75 to 4.1 (multiplet, 2H), 4.22 (s, 1H), 5.42 (s) and about 5.3 to 5.6 (broadened AB-q) together 3H; 6.65 to 7.35 (q-like, J≈8.5 cps. 4H).

The physico chemical properties are identical to those of the compound prepared in Example 5 of commonly assigned U.S. Pat. No. 4,067,986.

EXAMPLE 2 sodium potassium double salt of D-6{α-[3-(hydroxyethoxy)-phosphinyl)-ureido]-p-hydroxybenzylcarboxamido}-penicillanic acid The procedure of Example 1 was repeated but instead of sodium 2-ethylhexanoate, 10 g (0.10 mole) of potassium acetate dissolved in butanol were added. A precipitate was slowly formed and was treated with sodium bicarbonate in the manner in Example 1 to obtain 26 g (45% yield) of the sodium potassium double salt of D-6{α-[3-(hydroxyethoxy)- phosphinyl)-ureido]-p-hydroxybenzylcarboxamido}-penicillanic acid having physico chemcial properties identical to those of the disodium salt of Example 1.

EXAMPLE 3

The disodium salt of Example 1 was also prepared by using a sodium stearate suspension in acetone in place of the sodium 2-ethylhexanoate. A white powder was obtained consisting of the monosodium salt containing a fair amount of sodium stearate. 3.3 g of this product were suspended in 30 ml of water at 0° C. and the suspension was cooled by the exterior application of ice and by nitrogen being bubbled through the mixture. By addition of a 1 N sodium hydroxide solution to obtain a pH-value of 7, the precipitate obtained was dissolved. 90 ml of ethanol and 1.2 g of activated carbon were added thereto and the reaction mixture was stirred at 0° C. for ½ hour and was filtered. The filtrate was concentrated in vacuo (bath temperature not exceeding 20° C.) during which 2 portions of 80 ml of dry ethanol were added to remove as much water as possible. When concentrated to about 15 ml, the residue was with stirring, poured into a mixture of 55 ml of 2,2-dimethoxypropane and 120 ml of acetone. The resulting precipitate was filtered off, was washed with acetone and was dried in vacuo to obtain 2,4 of the disodium salt of Example 1.

EXAMPLE 4 disodium salt of D-6{α[-3-(hydroxy(ethoxy)phosphinyl)ureido]-p-hydroxybenzylcarboxamido}-penicillanic acid 108.5 g (0.2975 mole) of D-6-(α-amino)-p-hydroxybenzylcarboxamidopenicillanic acid (amoxicillin) was silylated with a solution of 162.5 ml (0.655 mole) of N,O-bistrimethylsilylacetamide in 750 ml of methylene chloride. After cooling the solution to about −70° C., a solution of 50.5 g (0.2975 mole) of ethyl chlorophosphorus isocyanatidate in 750 ml of ethylacetate was added dropwise. After completion of the addition, the mixture was stirred for 1.5 hours and 25 ml (1.39 mole) of water and 1 L of ethylacetate were then added at a temperature of −70° C. The temperature was allowed to rise to −40° C. in 1 hour and then to 0° C. in 1.5 hours. After separation of the layers, the organic layer was washed twice with 200 ml of water. Then 600 ml of 1 N sodium hydroxide were added slowly at a pH-value of 5 or slightly lower. After completion of the addition, the pH-value of the water layer was adjusted to 7 with 1 N sodium hydroxide in 1 hour. The solution was treated with 10 g of activated carbon and after filtration, was concentrated in vacuo during which several portions of dry ethanol were added in order to remove as much water as possible. The residue was dissolved in 1.5 L of methanol and the solution was concentrated in the same manner to 750 ml after which ethanol was slowly added during the concentration, thus keeping the volume at 750 ml until almost all the methanol was removed. The precipitate formed was filtered off, was washed with ethanol and diethyl ether and dried in vacuo over phosphorus pentoxide to obtain 100 g (60% yield) of the disodium salt of D-6-{α[-3-(hydroxy(ethoxy)phosphinyl)ureido}-p-hydroxybenzyl-carboxamido]-penicillanic acid.

EXAMPLE 5 disodium salt of D-6-{α-[3-hydroxy(ethoxy)phosphinyl)ureido]benzylcarboxamido}-penicillanic acid 10.5 g (0.03 mole) of D-6-(α-amino)benzylcarboxamido-penicillanic acid (ampicillin) was silylated with a solution of 9.6 ml (0.04 mole) of N,O-bistrimethylsilylacetamide in 50 ml of dry methylene chloride and the solution was cooled to −65° C. A solution of 5 g (0.03 mole) of (C$_2$H$_5$O)PO(Cl)NCO (ethyl chlorophosphorus isocyanatidate) in 55 ml dry methylene chloride was added thereto dropwise and the mixture was stirred for 75 minutes. Then, a mixture of 1.26 ml (0.07 mole) of water, 2.4 ml (0.03 mole) of pyridine and 30 ml of acetone was added thereto and after completion of the addition, the temperature was rapidly raised to −35° C. and then slowly to 0° C. over a period of 2 hours. A solution of 4.9 g (0.03 mole) of sodium 2-ethylhexanoate in 30 ml of dry acetone was added to the reaction mixture at 0° C. and the mixture was stirred for 1½ hours with the temperature being allowed to rise to about ambient temperature. A precipitate was formed which was filtered off and was suspended in 150 ml of dry acetone. The suspension was stirred for 45 minutes and the precipitate was filtered off. This procedure was repeated again and the precipitate obtained was suspended in 100 ml of water. The suspension was cooled with ice while nitrogen was bubbled through the mixture and the precipitate was dissolved by addition of an amount of sodium bicarbonate just sufficient for the desired salt formation. The solution obtained was freeze-dried resulting in 8.6 g (53% yield) of the disodium salt of D-6-{α-[3-hydroxy(ethoxy)phosphinyl)ureido]benzyl-carboxamido}-penicillanic acid having the following physico-chemical properties:

IR Spectrum (KBr-disc, values in cm$^{-1}$): ±3550, ±2600, +3320 and ±3250, 1780, 1740–1710, 1640–1670, ±1530 (intense), 1210, 1040, 700.

PMR Spectrum (d$_6$-DMSO, 60 Mc, δ-values in ppm, DDS as reference): 1.2 (t, J≈7.0 cps, 3H), 1.44 and 1.58 (6H), 3.95 (multiplet) and 4.24 (s) together 3H, about 5.5 (multiplet, J$_{5.6}$≈4.0 cps) and about 5.65 (d) together 3H, about 7.4 (5H), 7.7 (d, J≈8.5 cps) 7.9 (d, J≈7.5 cps), 9.15 (d, J≈7.5 cps).

EXAMPLE 6 disodium salts of other hydroxyphosphinylureidobenzylpenicillins

Using the procedure of Examples 1 or 3, the following compounds were prepared in yields varying from 35 to 65%;

Disodium salt of D-6-{α-[3-(hydroxy(methoxy)-phosphinyl)ureido]-p-hydroxybenzylcarboxamido}-penicillanic acid having the following physico chemical properties:

IR Spectrum (KBr-disc, values in cm$^{-1}$): about 3280–3600 (broad and intensive), ±2905 (sh), 1760, 1680 (sh), about 1645 to 1665, ±1600, ±1540, 1500, 1455, 1395, 1370 (sh), 135 (sh), 1310–1330, 1215–1245, 1180 (sh), 1125, 1080 (intensive), 1045, 895, ±770.

PMR Spectrum (about 5:1 mixture of d$_6$-DMSO and DCO$_2$D, 60 Mc, DSS as reference, δ-values in ppm): 1.47 and 1.59 (6H), 3.50 (d, J≈11.6 cps, 3H), 4.27 (s, 1H), 5.44 (s) and about 5.35 to 5.6 (broadened AB-q) together 3H, 6.7 to 7.35 (q-like, 4H).

Disodium salt of D-6-{α-[3-(hydroxy(benzyloxy)-phosphinyl)ureido]-p-hydroxybenzylcarboxamido}-penicillanic acid having the following physico chemical properties:

IR Spectrum (KBr- disc, values in cm$^{-1}$): about 3100–3600, shoulders at ±3050, 2970 and 2935, 1765, 1690 (sh), 1640–1660, 1595–1615, ±1550 (sh), 1515, 1455, 1400, 1380 (sh), 1320–1340, 1220–1260, 1180, 1135, 1090 (intensive), 1010–1035, 985, 900, 870, 845, 750, 710.

PMR Spectrum (about 4:1 mixture of d$_6$-DMSO and DCO$_2$D, 60 Mc, DSS, δ-values in ppm): 1.48 and 1.60 (6H), 4.26 (s, 1H), 4.86 (d, J≈7.0 cps, 2H), 5.45 (s) and 5.35 to 5.60 (AB-q, J≈4.0 cps) together 3H); 6.65 to 7.3 (q-like, J≈8.2 cps) and about 7.35 together 9H.

Thin layer chromatography-Rf+about 0.9 (UV positive) (silica, 95:5:5 mixture of methanol, acetic acid and water).

Disodium salt of D-6-{α-[3-(hydroxy(phenoxy)phosphinyl)ureido]-p-hydroxybenzylcarboxamido}penicillanic acid having the following physico chemical properties:

IR Spectrum (KBr-disc, values in cm$^{-1}$): 3400, 1780, 1660, 1610, 1520, 1400, 1320, 1220, 1140, 1060, 780, 700.

PMR Spectrum (mixture of d$_6$-DMSO and DCO$_2$D, δ-values in ppm, TMS as reference): 1.45 (s, 3H), 1.58 (s, 3H), 4.25 (s, 1H), 5.3–5.6 (multiplet, 3H), 6.75 (d, 2H) and 7.1–7.4 (multiplet, 7H).

The physio chemical properties of the three above-mentioned compounds are identical to those of the compounds prepared in Examples 5, 6 and 10 of U.S. Pat. No. 4,067,986.

EXAMPLE 7 trisodium salt of D-6-{α-[3-(dihydroxyphosphinyl)ureido]-p-hydroxybenzylcarboxamido}-penicillanic acid 2.17 g (5.95 mmoles) of D-6-(α-amino)-p-hydroxybenzylcarboxamido-penicillanic acid (amoxicillin) were silylated with a solution of 3.24 ml (13.1 mmoles) of N,O-bistrimethylsilylacetamide in 15 ml of methylene chloride and after cooling in the solution to about −75° C., a solution of 0.95 g (5.95 mmoles) of dichloro phosphorus isocyanatidate in 15 ml of ethyl acetate was added dropwise over one hour. After completion of the addition, the mixture was stirred for 1½ hours and a mixture of 0.96 ml (11.9 mmoles) of pyridine and 15 ml of ethyl acetate was added thereto followed by the addition of 0.69 ml (38 mmoles) of distilled water at a temperature of −70° C. The temperature of the reaction mixture was allowed to rise to −40° C. in one hour and from −40° to 0° C. in 1½ hours. At that temperature, the reaction mixture was washed 3 times with 25 ml portions of acidified water with a pH-value of 1.5. Then, 25 ml of water were added thereto and the pH-value was slowly adjusted to 7 with 1 N sodium hydroxide. The layers formed were separated and the aqueous layer was freeze-dried to obtain 3.0 g of a powder of trisodium salt of D-6-{α-[3-(dihydroxyphosphinyl)ureido]-p-hydroxybenzylcarboxamido}-penicillanic acid with a purity of 80%.

Various modifications of the process of the invention may be made without departing from the spirit or scope thereof and it is to be understood that the invention is intended to be limited only as defined in the appended claims.

We claim:

1. A process for the preparation of a compound of the formula

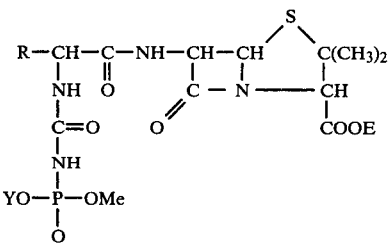

wherein R is phenyl optionally substituted with one to two members which may be the same or different selected from the group consisting of hydroxy, lower alkyl and lower alkoxy, Y is selected from the group consisting of Me, lower alkyl, aryl(lower)alkyl and aryl in which the aryl is optionally substituted by at least one alkyl, Me is a metal cation and E is selected from the group consisting of hydrogen and a metal cation which may be the same or different from the metal cation Me, comprising reacting a compound of the formula

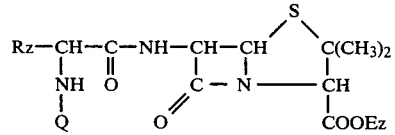

wherein Q is selected from the group consisting of hydrogen atom and silicon atom carrying substituents selected from the group consisting of lower alkyl, lower haloalkyl, aryl, aralkyl and lower alkoxyalkyl and halogen, Rz has the same significance as R as defined above with the proviso that any hydroxy group(s) present on the phenyl group are replaced by —OQz wherein Qz is a silicon atom carrying substituents selected from the group consisting of lower alkyl, lower haloalkyl, aryl, aralkyl and lower alkoxyalkyl and halogen and Ez is a carboxyl protecting group with a compound of the formula

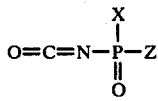

wherein Z is halogen, and X is selected from the group consisting of OY and Z at a temperature below 0° C. under anhydrous conditions in an organic solvent medium, carefully hydrolyzing the resulting product thus either with an amount of water just sufficient to remove any protecting groups present in the intermediate product and to hydrolyze Z to hydroxy and, still under anhydrous or substantially anhydrous conditions, converting hydroxy formed by hydrolysis of Z into OMe, wherein Me is as defined above by reaction with an organic acid salt having a salt-forming cation Me or in the case wherein the organic solvent used in insoluble or substantially insoluble in water, with an excess of water, washing the mixture with water at a pH-value of 0 to 3 extracting the organic layer formed with water at a pH-value of 5 to 8 by adding a hydroxide or a salt having a salt-forming cation Me to convert hydroxy formed by hydrolysis of Z into OMe and Ez into Me wherein Me is as defined above.

2. The process of claim 1 wherein the organic acid salt is a salt of an alkanoic acid of 1 to 20 carbon atoms.

3. The process of claim 2 wherein the alkanoic acid has 5 to 10 carbon atoms.

4. The process of claim 1 wherein the excess water is 25 to 60% excess.

5. The process of claim 1 wherein the pH value of the wash water is 1 to 2.

6. The process of claim 1 wherein the temperature for the reaction is between −90° to −40° C.

7. The process of claim 6 wherein the temperature is −80° to −60° C.

8. The process of claim 1 wherein Q is trimethylsilyl.

9. The process of claim 1 wherein Z is chlorine.

10. The process of claim 1 wherein E and Me are selected from the group consisting of alkali metal and alkaline earth metal.

11. The process of claim 10 wherein E and Me are selected from the group consisting of sodium, potassium and calcium.

12. The process of claim 2 wherein the alkanoic acid is selected from the group consisting of acetic acid, propionic acid, butyric acids, pentanoic acids, hexanoic acids, octanoic acids and stearic acid.

13. The process of claim 2 wherein the alkanoic acid is 2-ethyl hexanoic acid.

14. The process of claim 1 wherein the salt formation is effected in a moderately polar organic solvent.

* * * * *

UNITED STATES PATENT AND TRADEMARK OFFICE
CERTIFICATE OF CORRECTION

PATENT NO. : 4,177,189

DATED : Dec. 4, 1979

INVENTOR(S) : Piet J. Akkerboom, Geertruida J. Lower & Willem J. Timp

It is certified that error appears in the above-identified patent and that said Letters Patent are hereby corrected as shown below:

In the Abstract and in Claim 1 the formula should be

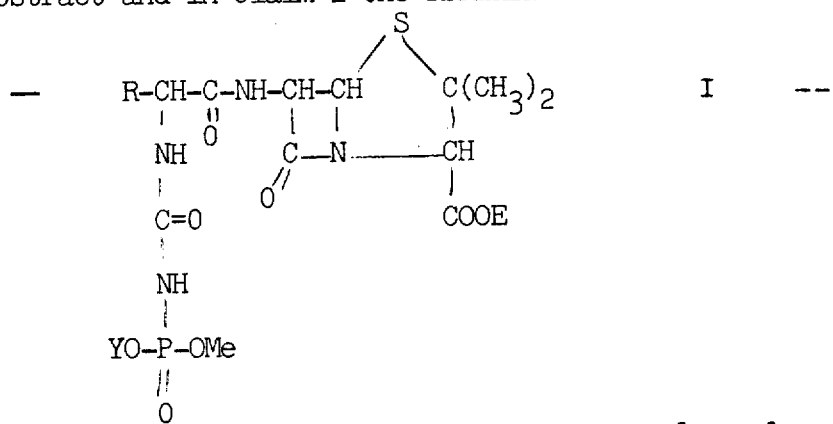

Signed and Sealed this

Twenty-second Day of July 1980

[SEAL]

Attest:

SIDNEY A. DIAMOND

Attesting Officer

Commissioner of Patents and Trademarks